US009414787B2

(12) United States Patent
Montambeau et al.

(10) Patent No.: US 9,414,787 B2
(45) Date of Patent: Aug. 16, 2016

(54) NAVIGATION FEATURES FOR ELECTROCARDIOGRAPH DEVICE USER INTERFACE

(71) Applicant: Welch Allyn, Inc., Skaneateles Falls, NY (US)

(72) Inventors: Elaine Carole Montambeau, Syracuse, NY (US); Kathryn Coles, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 14/086,326

(22) Filed: Nov. 21, 2013

(65) Prior Publication Data

US 2015/0141862 A1    May 21, 2015

(51) Int. Cl.
*A61B 5/04* (2006.01)
*A61B 5/00* (2006.01)
*A61B 5/044* (2006.01)
A61B 5/0245 (2006.01)

(52) U.S. Cl.
CPC ............... *A61B 5/748* (2013.01); *A61B 5/044* (2013.01); *A61B 5/743* (2013.01); *A61B 5/7435* (2013.01); A61B 5/0245 (2013.01)

(58) Field of Classification Search
CPC ..... A61B 5/044; A61B 5/0432; A61B 5/0006
USPC ........................................ 600/523, 509, 508
See application file for complete search history.

(56) References Cited

U.S. PATENT DOCUMENTS 4,883,065 A    11/1989  Kelen
5,735,285 A     4/1998  Albert et al.
(Continued)

FOREIGN PATENT DOCUMENTS

WO    2008070793 A2    6/2008
WO    2013089712 A1    6/2013

OTHER PUBLICATIONS

Infiniti ECG Scanning Software, Lifescreen ECG Instruction Manual Software 2.03, accessed at http://www.infiniti.se/upload/Bruksanvisningar/DMR/SPA_UM_EN_Lifescreen_English_18-0020%20Lifescreen%20Instruction%20Manual%20Rev%20C.pdf, accessed on Jul. 1, 2013, 61 pages.
(Continued)

*Primary Examiner* — Amanda Patton
*Assistant Examiner* — Philip C Edwards
(74) *Attorney, Agent, or Firm* — Merchant & Gould P.C.

(57) ABSTRACT

An electrocardiograph device and methods of navigating displays of such a device are disclosed. In one example, an electrocardiograph device includes a display, a plurality of electrocardiograph signal leads, and a programmable circuit. The programmable circuit is configured to receive electrical signals via the electrocardiograph signal leads representative of a heartbeat of a patient. The programmable circuit is configured to generate a user interface to be presented on the display, the user interface comprising a lead display including a screen layout including a plurality of waveform regions. The waveform regions display a waveform corresponding to an electrical signal from one of the leads over a time interval including at least one heartbeat period. Selection of a region causes display of an extended waveform region displaying a waveform over a second time interval that is longer than the first time interval, and which includes a plurality of heartbeat periods.

15 Claims, 15 Drawing Sheets

(56) References Cited

U.S. PATENT DOCUMENTS

| | | | |
|---|---|---|---|
| 6,149,602 | A | 11/2000 | Arcelus |
| 6,654,631 | B1 | 11/2003 | Sahai |
| 6,788,969 | B2 | 9/2004 | Dupree et al. |
| 6,934,578 | B2 * | 8/2005 | Ramseth ............... 600/523 |
| 7,113,820 | B2 | 9/2006 | Schlegel et al. |
| 7,894,885 | B2 | 2/2011 | Bartal et al. |
| 8,209,000 | B2 | 6/2012 | Kuo et al. |
| 8,241,212 | B2 | 8/2012 | Li et al. |
| 2003/0208128 | A1 | 11/2003 | Hamilton et al. |
| 2004/0054294 | A1 | 3/2004 | Ramseth |
| 2006/0167367 | A1 * | 7/2006 | Stanczak et al. ....... 600/523 |
| 2008/0146954 | A1 | 6/2008 | Bojovic et al. |
| 2012/0143031 | A1 | 6/2012 | Belalcazar et al. |

OTHER PUBLICATIONS

Anslab, Electrocardiography accessed at http://www.anslab.net/static/helpprofessional/cardiography.html, accessed on Jul. 1, 2013, 5 pages.

ECG Implementation on the TMS320C5515 DSP Medical Development Kit (MDK), Vishal Markandey, Application Report SPRAB36B-Jun. 2010; accessed at http://www.ti.com/general/docs/lit/getliterature.tsp?literatureNumber=sprab36b&fileType=pdf, accessed on Jul. 1, 2013, 35 pages.

* cited by examiner

NAVIGATION FEATURES FOR ELECTROCARDIOGRAPH DEVICE USER INTERFACE

BACKGROUND

An electrocardiograph ("ECG") is a representation of the electrical signals generated by the heart muscle. Typical ECG devices derive one or more ECG waveforms by measuring small voltages that appear on pickup electrodes, or leads, placed on the surface of a patient's body. Electrocardiograph (ECG) machines typically include a display device, a plurality of electrodes, and control and signal conditioning circuitry. The electrodes are designed to be attached to the skin on the chest and limbs of a patient based on a 12-lead placement model. Generally, limb lead electrodes are placed on each arm and on the left leg, while precordial lead electrodes are placed on the left upper chest region over the heart in close proximity to the heart and at a location of strongest ventricular cardiac action potential signal strength. The display device presents a waveform representative of an electrical signal of each of the 12 leads, typically within a small window showing one or a small number of periodic intervals (e.g., approximately a single heartbeat cycle), based on detection of such signals by the control circuitry.

Because ECG devices typically present each of the 12 leads on a display, each waveform for each of the leads is typically restricted within a small region of the display. Typically, this is acceptable, since users of ECG devices can view a single heartbeat period within such a small region. However, in some cases, use of such small regions of a display is unacceptable. For example, it may be difficult, within such a small display region, to determine variations in a signal occurring over multiple heartbeat periods, such as drift of the electrical signal to a higher or lower voltage, which may indicate an issue with either the device or patient. In existing machines, to view an extended version of one of the waveforms, the user must navigate a series of configuration screens to reconfigure a display. To return to the screen displaying each of the 12 leads, the user must again navigate a series of configuration screens. Such reconfiguration of displays is time-intensive, and cumbersome.

SUMMARY

In summary, the present application relates to navigation features for a user interface of an electrocardiograph device. In example aspects, various regions of the display can be selected to display additional information regarding a particular electrical lead of an electrocardiograph device, or to display additional details regarding connection of such leads to a patient, or to scroll through possible views available for reviewing the signals at various ECG leads.

In a first aspect, an electrocardiograph device includes a display, a plurality of electrocardiograph signal leads configured for electrical connection to a patient, and a programmable circuit operatively connected to the display and to the plurality of electrocardiograph signal leads. The programmable circuit is configured to receive electrical signals via the electrocardiograph signal leads representative of a heartbeat of a patient. The programmable circuit is further configured to generate a user interface to be presented on the display, the user interface comprising a lead display including a screen layout including a plurality of waveform regions, the waveform regions being adjacent to one another and each displaying a waveform corresponding to an electrical signal from one of the plurality of electrocardiograph signal leads over a first time interval including at least one heartbeat period. The programmable circuit is also configured to, upon receiving selection of a region of the user interface, display an extended waveform region associated with one or more of the electrocardiograph signal leads, the extended waveform region displaying a waveform corresponding to the electrical signal from one of the plurality of electrocardiograph leads over a second time interval that is longer than the first time interval, and which includes a plurality of heartbeat periods.

In a second aspect, an electrocardiograph device includes a display, a plurality of electrocardiograph signal leads configured for electrical connection to a patient, and a programmable circuit operatively connected to the display and to the plurality of electrocardiograph signal leads. The programmable circuit is configured to receive electrical signals via the electrocardiograph signal leads representative of a heartbeat of a patient. The programmable circuit is further configured to generate a user interface to be presented on the display, the user interface comprising a lead display including a screen layout including a plurality of regions, the plurality of regions being adjacent to one another and each displaying an indication of an electrical signal from one or more of the plurality of electrocardiograph signal leads. The programmable circuit is also configured to, upon receiving selection of a region of the user interface, displaying an extended region associated with one or more of the electrocardiograph signal leads, the extended region at least partially overlaying one or more remaining regions adjacent to the selected region.

In a third aspect, a method of operating an electrocardiograph device includes attaching a plurality of electrocardiograph signal leads to a patient, and selecting a display mode on a display of the electrocardiograph device to display a lead display including a screen layout including a plurality of regions, the plurality of regions being adjacent to one another and each displaying an indication of an electrical signal from one or more of the plurality of electrocardiograph signal leads. The method also includes selecting one of the plurality of regions on the display, thereby causing the electrocardiograph device to display an extended region associated with one or more of the electrocardiograph signal leads, the extended region at least partially overlaying one or more remaining regions adjacent to the selected region.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

DETAILED DESCRIPTION

As briefly described above, embodiments of the present invention are directed to navigation features for a user interface of an electrocardiograph device. In example aspects, various regions of the display can be selected to display additional information regarding a particular electrical lead of an electrocardiograph device, or to display additional details regarding connection of such leads to a patient, or to scroll through possible views available for reviewing the signals at various ECG leads. As discussed herein, the navigation features provided by way of the present disclosure simplify navigation among views provided by an electrocardiograph machine simplify the manner in which views can be changed on a display of such a device, thereby saving time and improving the usability of such devices.

Figure 1:
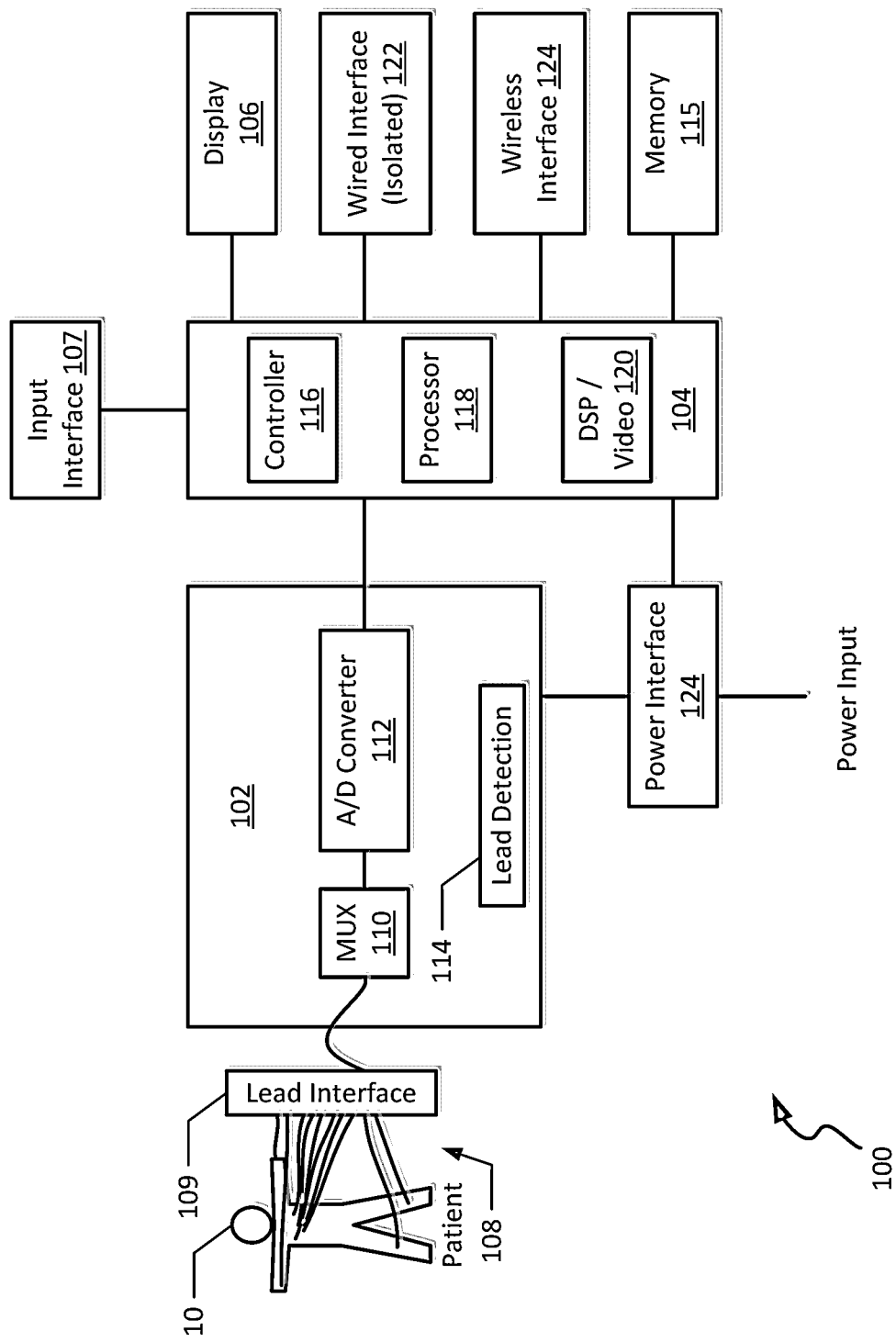
FIG. 1 is a block diagram of an example electrocardiograph device useable for detecting cardiac signals of a patient, according to a possible embodiment of the present disclosure.

Referring now to FIG. 1, a schematic block diagram of an example electrocardiograph (ECG) device 100 is shown in association with a patient 10. The ECG device includes a patient interface 102, processing system 104, and display 106.

The patient interface 102 connects to a plurality of electrocardiograph signal leads 108, which are electrically connected to a patient 10 to capture electrical signals generated based on a cardiac rhythm of the patient. In example embodiments, the patient interface 102 includes a multiplexor 110 useable to aggregate signals from a lead interface 109, and route such signals to an electrical interface 112, such as a A/D conversion circuit. A lead detection circuit 114 determines whether each of the leads 108 are electrically connected to a patient, such as to determine issues with electrical connection (thereby flagging, for a caregiver, that an electrical signal is not representative of the patient's cardiac rhythm due to connectivity issues).

The processing system 104 receives the collected digital signals from the patient interface 106, and performs a variety of processing tasks on those signals. For example, the processing system 104 is communicatively connected to a memory 115. The memory 115 stores various types of data and/or software instructions that, when executed by the processing system 104, cause the ECG device 100 to perform ECG processing and display tasks, as well as storage and communication of ECG-related data.

In various embodiments, the memory 115 can be implemented as any of a variety of types of computer-readable media or computer storage media incorporated into a computer storage device or system. In accordance with the present disclosure, the term computer readable media as used herein may include computer storage media and communication media. As used in this document, a computer storage medium is a device or article of manufacture that stores data and/or computer-executable instructions. Computer storage media may include volatile and nonvolatile, removable and non-removable devices or articles of manufacture implemented in any method or technology for storage of information, such as computer readable instructions, data structures, program modules, or other data. By way of example, and not limitation, computer storage media may include dynamic random access memory (DRAM), double data rate synchronous dynamic random access memory (DDR SDRAM), reduced latency DRAM, DDR2 SDRAM, DDR3 SDRAM, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. Computer storage media does not include a carrier wave or other propagated or modulated data signal.

In the embodiment shown, the processing system 104 includes a controller 116, processor 118, and signal processing circuit 120. The controller 116 is configured for controlling peripheral devices (e.g., input devices and output devices, such as the display 106 and input device 107 discussed below). Optionally, the controller 116 can correspond to a communication controller, useable for managing wired and/or wireless communications via communication interfaces, such as wired communication interface 122 and wireless communication interface 124, respectively. The wired communication interface 122 can be implemented, for example, as an Ethernet interface, a token-ring network interface, a fiber optic network interface, or other wired interface, such as a Universal Serial Bus (USB) connector. The wireless communication interface 124 can, for example, be implemented according to a desired wireless communication protocol (e.g., WiFi, WiMax, etc.).

The processor 118 generally coordinates operations of the ECG device based on operating software stored in the memory 115, and coordinates interaction between the patient interface 102 and display 106. The signal processing circuit 120 performs digital signal processing and video processing operations on received signals from the patient interface 102 to prepare received signals for display via the controller 116 and display 106.

The display 106 corresponds to a screen integrated with or communicatively connected to the ECG device 100. In various embodiments, the display 106 can be various types of devices for displaying video information, such as an LCD display panel, a plasma screen display panel, a touch-sensitive display panel, an LED screen, a cathode-ray tube display, or a projector. In some such embodiments, the display 106 can also function as an input device (e.g., a touch screen display). In some embodiments, in particular those in which display 106 is not a touch screen display, a further input device 107 can be included, such as a keyboard, pointer device, touchpad, or other input mechanism.

In addition, a power interface 124 provides a power source to the various other components of the ECG device 100, such as the patient interface 102 and processing system 104 (including display 106). In various embodiments, the power interface 124 can receive a power input (e.g., via a traditional 120 VAC plug, or a DC, battery, or other electrical power source).

It is noted that, in some embodiments, the ECG device 100 as discussed above can be incorporated into or with other types of diagnostic equipment; accordingly, although discussed herein as an ECG device specifically, it is understood that the above functionality, and the below graphical and navigational features, could be incorporated into a multi-function healthcare, diagnostic, or patient monitoring device.

Figure 2:
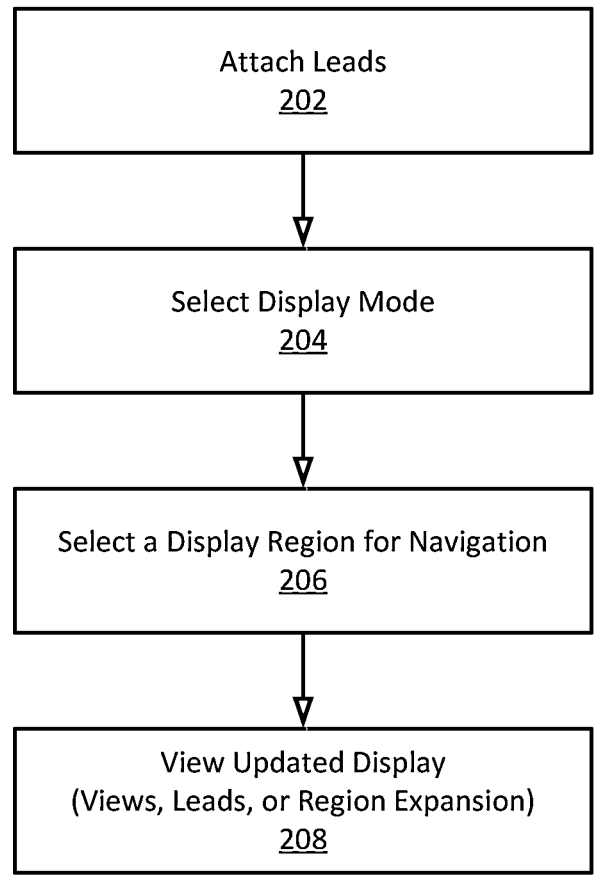
FIG. 2 is a flowchart of a method for operating an electrocardiograph device, according to an example embodiment of the present disclosure.
Figure 2:

Referring now to FIG. 2, an example flowchart of a method 200 for operating an electrocardiograph device, such as ECG device 100 of FIG. 1, is shown. In the example embodiment shown, the method 200 can be performed by a user of such a device, or can be performed by a user of a remote computer, or at least partially by the device or a computing system or device communicatively connected thereto.

In the embodiment shown, the method 200 includes an attachment operation 202, which corresponds to attaching electrocardiograph signal leads to a patient to be monitored. In operation 202, a user of the ECG device 100, such as a healthcare provider (a physician, nurse, or other clinical staff) can electrically connect such leads to the patient, thereby forming an electrical connection by which ECG device 100 can detect heartbeat signals.

Figure 3:
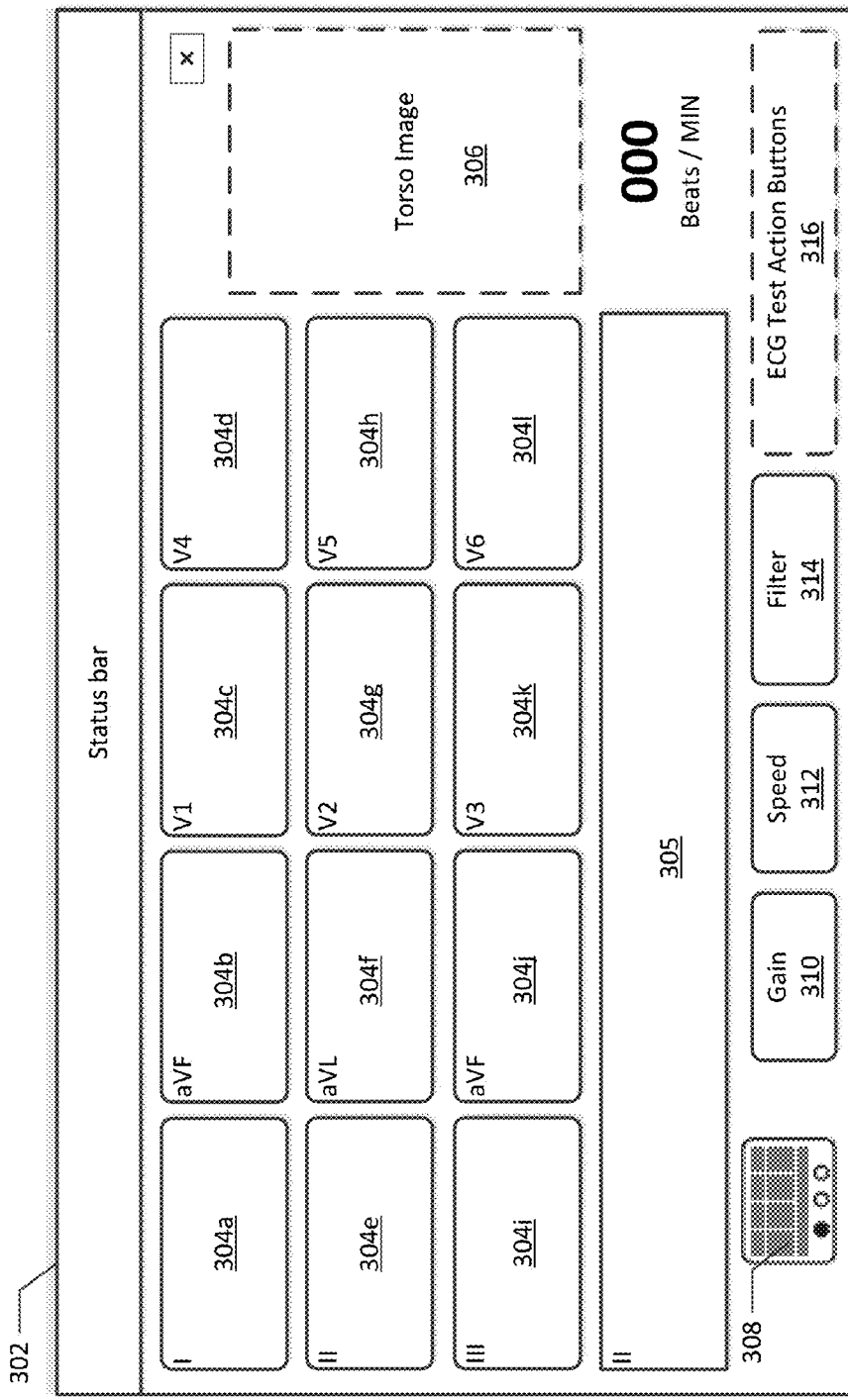
FIG. 3 is a schematic illustration of a lead display depicting a screen layout for a twelve-lead electrocardiograph device including a plurality of display regions, according to an example embodiment of the present disclosure.

A display mode selection operation 204 corresponds to the user selecting to display waveforms that are associated with the electrocardiograph signal leads in a particular configuration. This can include, for example, initializing the display (e.g., turning on the device) or can alternatively correspond to selecting a mode from a menu or based on a touch screen option presented by the ECG device 100. Generally, the display mode selection operation 204 can result in display of a screen layout that includes a number of waveform regions, including some that are adjacent one another. The waveform regions can each correspond to an electrical signal from the electrocardiograph signal leads, as illustrated in FIG. 3. As seen in FIG. 3, each of the displayed leads (or at a minimum, one or more of such leads) displays an electrocardiograph signal over a time interval that is at least one heartbeat period in length (duration).

A selection operation 206 corresponds to selection of at least one region of a displayed screen layout. The selection operation 206 can, in various embodiments, correspond to selection of (1) a region of the screen layout that includes a waveform representing one or more of the electrocardiograph signal leads, (2) selection of a navigation option, such as a view toggle button, a lead display selection button, or other navigation buttons, or (3) selection of a graphical representation of the patient to inspect various electrode connectivity issues. Selections of other graphical elements could be included as well. The selection can occur based, for example, upon touching the corresponding graphical element displayed on a touch sensitive display, or otherwise using a keypad or pointer to select such a graphical element.

A display update operation 208 is performed in response to the selection operation 206, and updates a display of an ECG device in response to the selected region. The display update operation 208 can have various effects. In some example embodiments, such as those described in connection with FIGS. 3-6 below, selection of a region of the screen layout that includes a waveform can cause expansion of the region to form an extended region in which a plurality of additional heartbeat periods are displayed. In such embodiments, a second subsequent selection of the extended region can cause the display to return to the original screen layout. Such a selectable expansion arrangement can be particularly useful in user interfaces in which waveform regions are displayed for each of the 12 electrocardiograph signal leads, such as in FIG. 3.

In an alternative embodiment, the display update operation 208 can be performed in response to a selection of a view toggle button, lead display selection button, or other types of buttons. In such embodiments, the display update operation 208 can correspond to toggling quickly among a plurality of preset views. In an example of such an arrangement, a view toggle button can be used to cycle among a plurality of different view layouts, with each view layout including a different combination of regions of varying sizes, and including a different combination of electrocardiograph signal leads. For example, one layout can include all 12 electrocardiograph signal leads, while a further layout could include a particular set of four or more of the electrocardiograph signal leads, but could include extended regions to display multiple heartbeat periods. Still further layouts could group signals from different electrocardiograph signal leads. An example of toggling using a view toggle button is provided below, in connection with FIGS. 11-15.

In accordance with this embodiment, a lead display selection button could also be used, in connection with views where fewer than all 12 electrocardiograph signal leads are displayed, to cycle among display of the plurality of electrocardiograph signal leads. For example, for views including waveforms from 4 of the leads, the leads display selection button would allow toggling among three screens, each of which would be configured to display a set of signals from 4 different electrocardiograph signal leads.

In a further alternative embodiment, the display update operation 208 can be configured to display an enlarged version of a graphic useable to assist with diagnosis of a patient. In example versions of such an embodiment, a graphic of a torso of a patient can be located within a region of the screen in one or more example layouts, and can, when selected, cause display of a larger version of such a graphic. This can allow a user to view proper placement of electrocardiograph signal leads on the patient, or can detect whether a signal is being properly received at the ECG device (e.g., by use of a different colored, or blinking, indicator within the graphic). One possible version of these embodiments is discussed below in connection with FIGS. 7-10.

Referring now to FIGS. 3-6, example lead displays are presented illustrating operation of one possible navigation feature useable in connection with an ECG device, such as device 100 discussed above. In particular, the example of FIGS. 3-6 represents selection of a particular region that includes a waveform showing at least about one heartbeat period to cause display of an expanded region that displays a plurality of heartbeat periods to show trends in the ECG signal.

Figure 4:
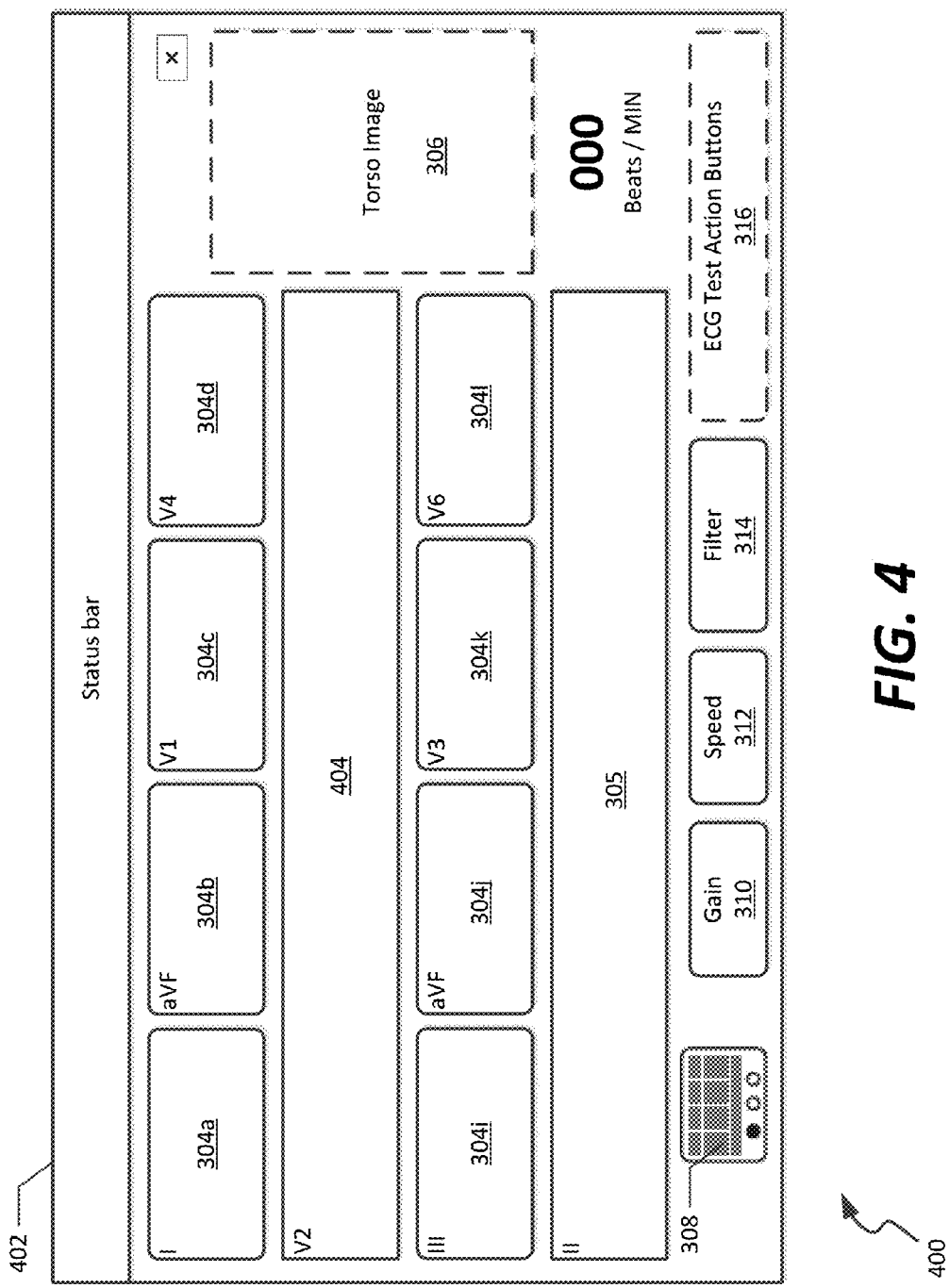
FIG. 4 is a schematic illustration of a lead display depicting a second screen layout including an extended region overlaying existing display regions, according to an example embodiment of the present disclosure.

FIGS. 3-4 illustrate a schematic version of use of such a navigational feature in connection with a lead display 300. As illustrated in FIG. 3, lead display 300 includes a screen layout 302 in which each of 12 different regions 304a-1 are displayed, each representing a different one of the plurality of electrocardiograph signal leads placed on a patient. In the embodiment shown, the screen layout 302 also includes an aggregate signal 305, as well as a torso image 306 of the patient, a view toggle button 308, a gain adjustment button 310, a speed adjustment button 312, and a filter button 314. The screen layout 302 further includes one or more ECG test action buttons 316, useable for diagnosis of perceived irregularities in a particular ECG signal.

As shown in FIG. 3, each of regions 304a-1 are placed in a 4×3 array, such that each of three rows has four columns of regions. Due to the screen layout, and based on horizontally extending waveforms in each of the regions 304a-1, the gain adjustment button 310, speed adjustment button 312, and filter button 314 can be used to adjust the window scaling in each region to ensure that at least one heartbeat period can be displayed within each region. Optionally, a heart rate indicator 320 can be included to illustrate to a user of the ECG device (e.g., a caregiver) a particular heart rate to assist with the scaling of a heart rate signal.

In FIG. 4, the lead display 300 is altered relative to FIG. 3, based on a selection of an example region. In the example shown, region 304g of FIG. 3 was selected, to expand that region to show additional heartbeat periods associated with that particular electrode.

Upon selection of region 304g, a updated, or second, screen layout 402 is displayed. The screen layout 402 is generally identical to that of FIG. 3, except that extended region 404 replaces region 304g. As shown, extended region 404 occupies an entire row to allow for display of a plurality of heartbeat periods. Accordingly, extended region 404 overlays a region previously occupied by regions 304e, 304f, and 304h (alongside region 304g). When region 404 is selected again by a user, the screen layout reverts to that shown in FIG. 3. Furthermore, if a region in a different row is selected, a similar functionality is provided in which an extended region can replace the various regions in that same row.

Figure 5:
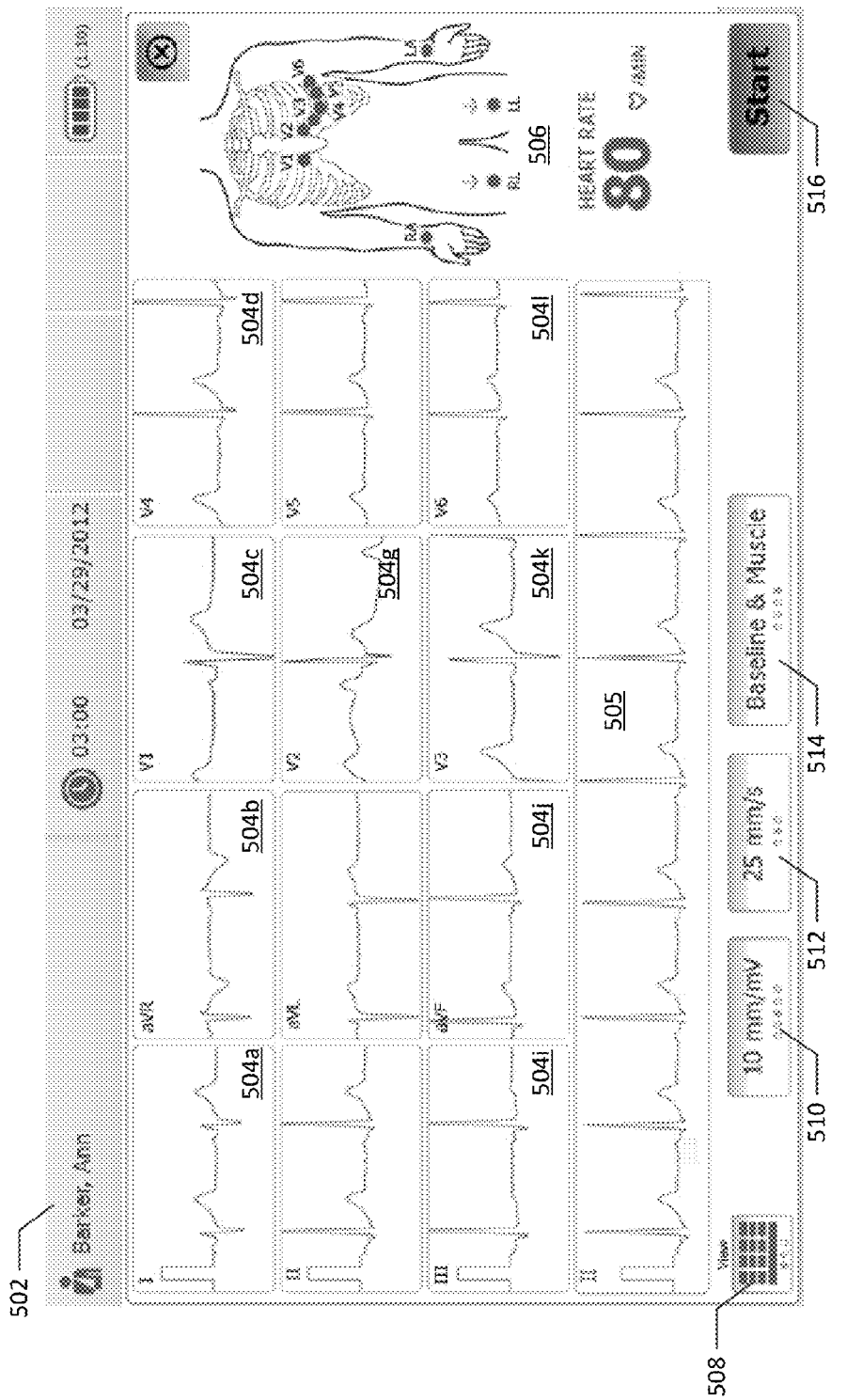
FIG. 5 is an example of a lead display depicting a screen layout for a twelve-lead electrocardiograph device as illustrated in FIG. 3.
Figure 6:
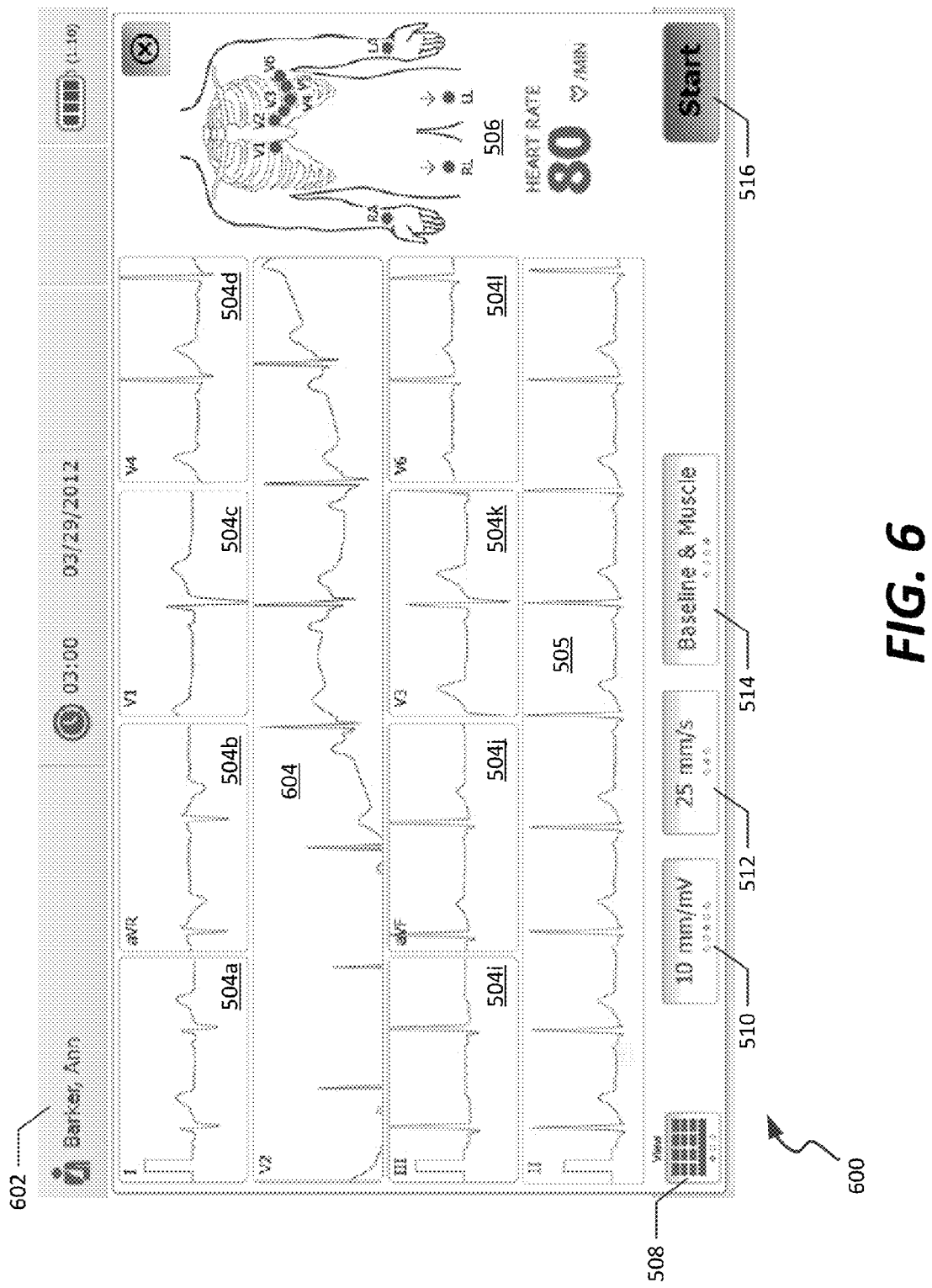
FIG. 6 is an example of a lead display depicting a screen layout for a twelve-lead electrocardiograph device as illustrated in FIG. 4.

A specific example of such a navigation feature is depicted in FIGS. 5-6. FIG. 5 illustrates a lead display 500 that generally corresponds to lead display 300 as depicted in FIG. 3, with a screen layout 502 that includes 12 different regions 504a-1 analogous to regions 304a-1 of FIG. 3. As seen in FIG. 5, each of regions 504e-h are positioned along a common baseline, such that each appears to be consistent in overall signal level. However, as illustrated in FIG. 6, a screen layout 602 illustrates that, upon selection of region 504g, an extended region 604 is displayed, showing a wandering baseline for the signals corresponding to the electrocardiograph signal leads displayed in region 504g. As such, as discussed above, at times, it is useful to display a plurality of heartbeat periods to detect issues such as signal drift, which is shown in region 604.

It is also noted that, in both FIGS. 5 and 6, a torso image 506 is displayed that includes an indication of the location of electrocardiograph signal leads. The torso image can include an indication of the specific lead that is being expanded, or can alternatively include an indication (e.g., by flashing, or changing color) in case a weak or erratic signal is received from a particular electrocardiograph signal lead. Additionally, a view toggle button 508, as well as a gain adjustment button 510, a speed adjustment button 512, and a filter button 514 can also be included, alongside a start ECG test button 516.

Figure 7:
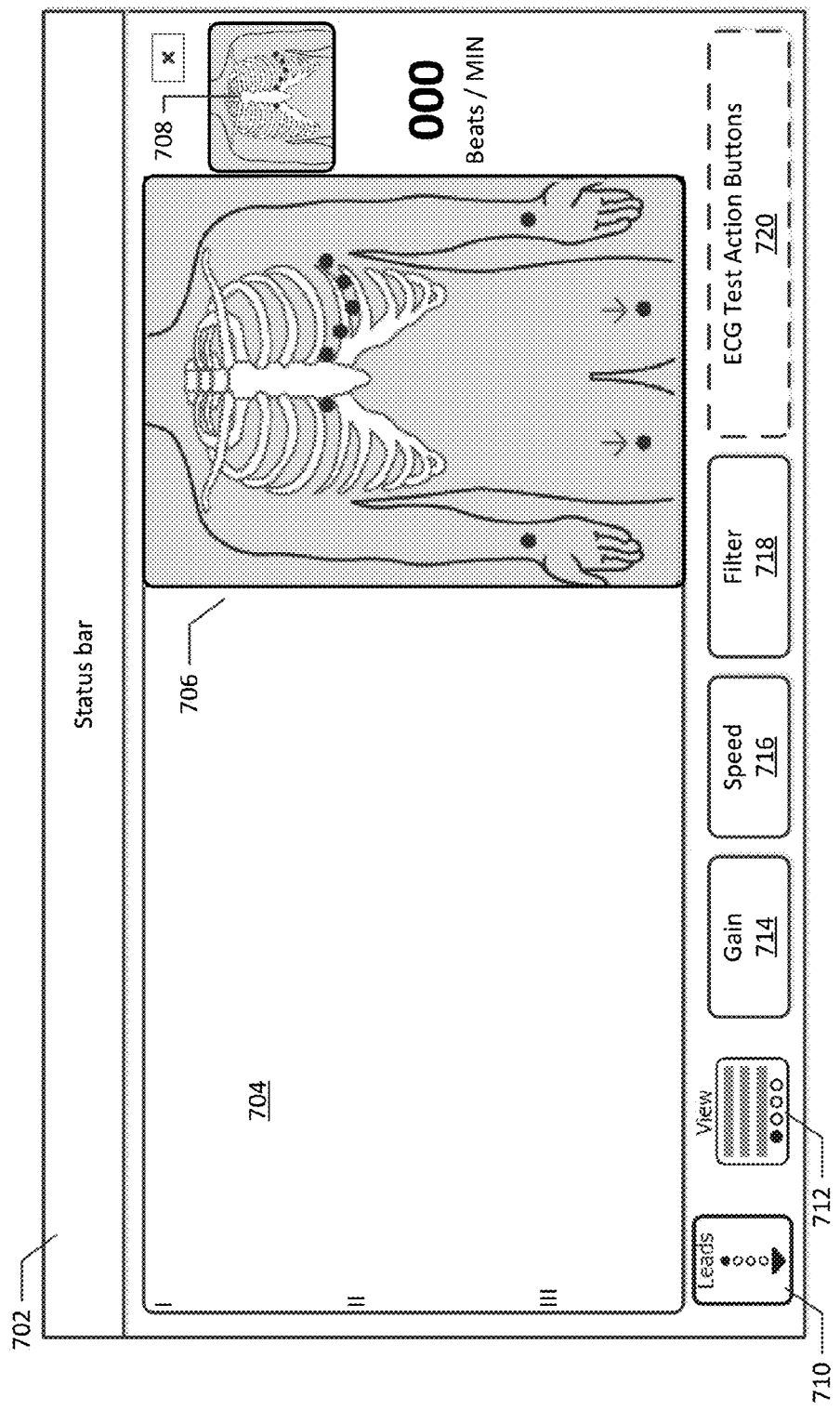
FIG. 7 is a schematic illustration of a lead display system depicting a screen layout including an expanded patient torso depiction, according to an example embodiment.

Referring now to FIGS. 7-10, screen layouts illustrating a second navigation feature are provided, in particular, for response to selection or deselection of a torso image. FIG. 7 illustrates a lead display 700 including a particular screen layout 702 in which three electrocardiograph signal leads are displayed in a common region 704. In this screen layout 702, an enlarged torso image 706 is positioned alongside the common region 704, with a miniaturized version of the torso image 708 located alongside the common region 704.

The screen layout 702 further includes a plurality of navigation and display features alongside a bottom edge of the common region 704, including a leads region 710, a view toggle button 712, a gain adjustment button 714, a speed adjustment button 716, and a filter button 718. The screen layout 702 further includes one or more ECG test action buttons 720, useable for diagnosis of perceived irregularities in a particular ECG signal.

Selection of the leads region 710 allows a user to cycle through different sets of electrocardiograph signal leads, such that each of the 12 leads can be displayed. Selection of the view toggle option 712 allows the user to view different layouts of electrocardiograph signal leads, as illustrated in FIGS. 11-15.

Figure 8:
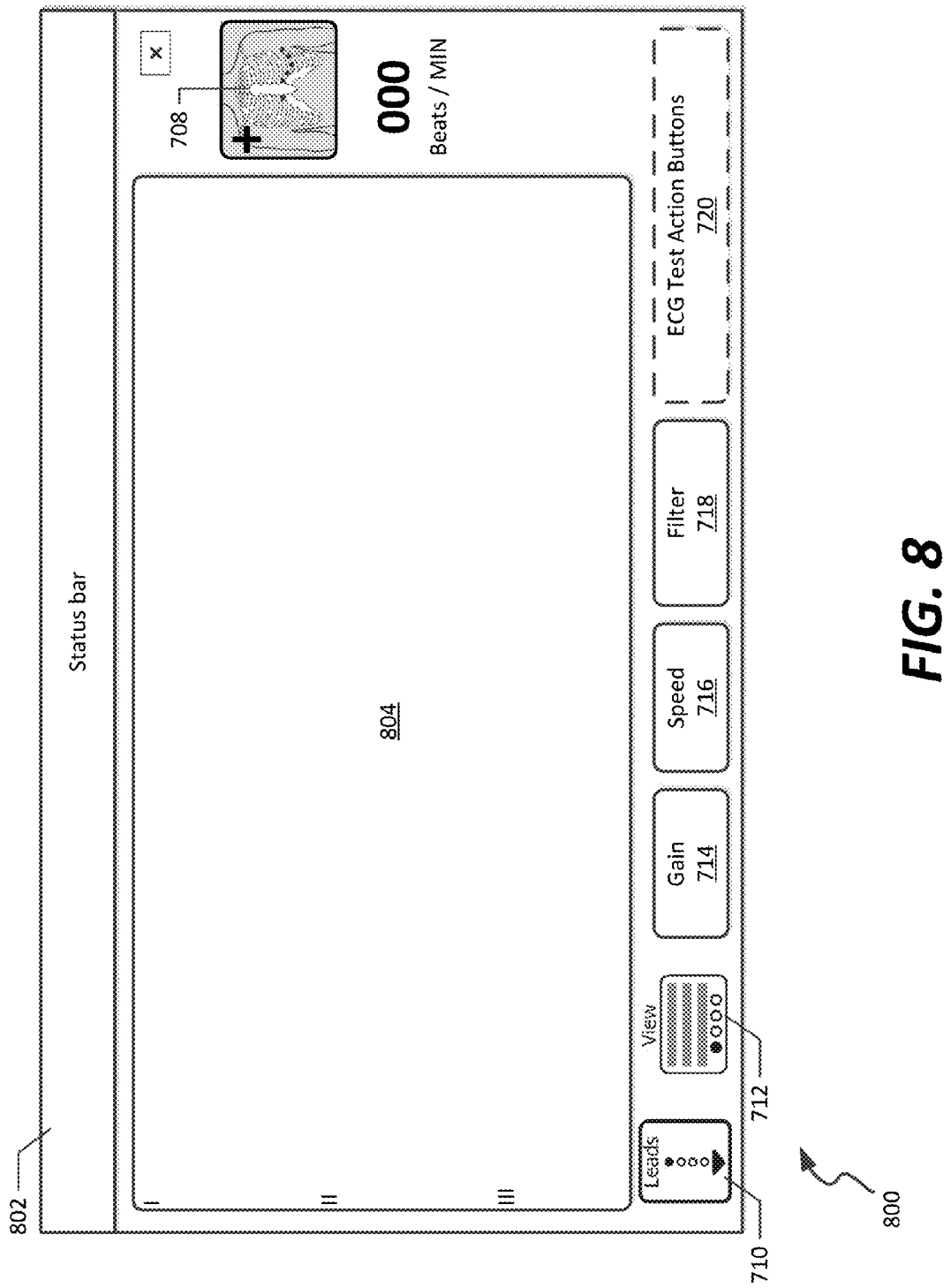
FIG. 8 is a schematic illustration of a lead display system depicting a screen layout including a minimized patient torso depiction, according to an example embodiment.

Referring to FIG. 8, the lead display 700 includes a second screen layout 802 that is shown upon selection of either of the enlarged torso image 706 or the miniaturized version of the torso image 708. As illustrated in FIG. 8, the enlarged torso image 706 is hidden, allowing for display of an enlarged common region 804, showing a longer portion of the waveforms. Selection of the miniaturized version of the torso image 708 causes the display to revert to the screen layout 702 shown in FIG. 7.

It is noted that, in the embodiments of FIGS. 7-10, the enlarged torso image 706 can provide additional detail relative to the miniaturized version of the torso image 708 regarding placement of the electrocardiograph signal leads, or whether such leads are operating correctly. As noted above, the indicators of leads on the enlarged torso image 706 may include all leads, wherein the image 708 may only include a subset of the leads; additionally, the enlarged torso image 706 may include additional detail or functionality, such as the indicators of correct placement previously discussed (e.g., changes in color or appearance).

Figure 9:
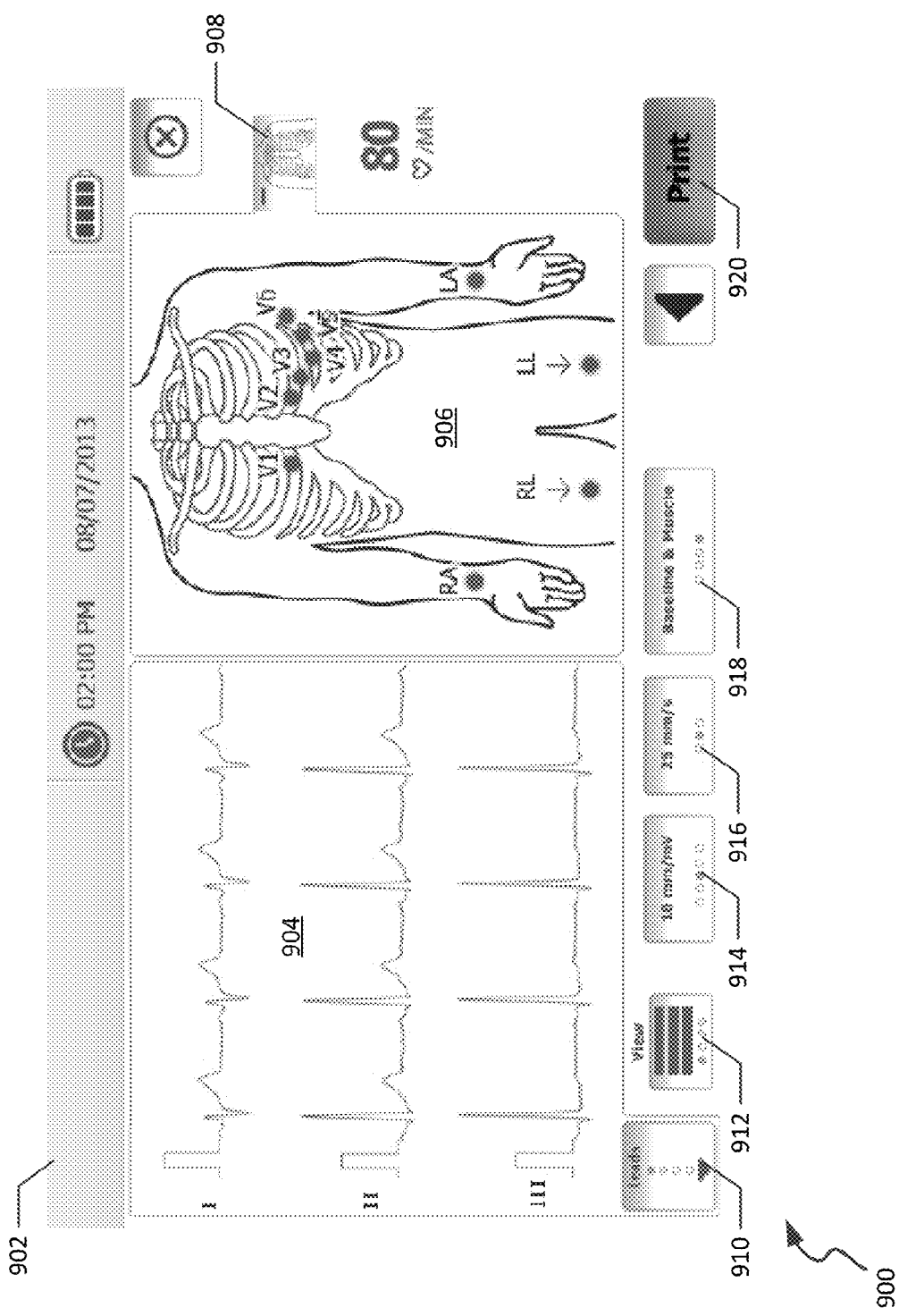
FIG. 9 is an example of the lead display system including an expanded patient torso depiction as in FIG. 7.
Figure 10:
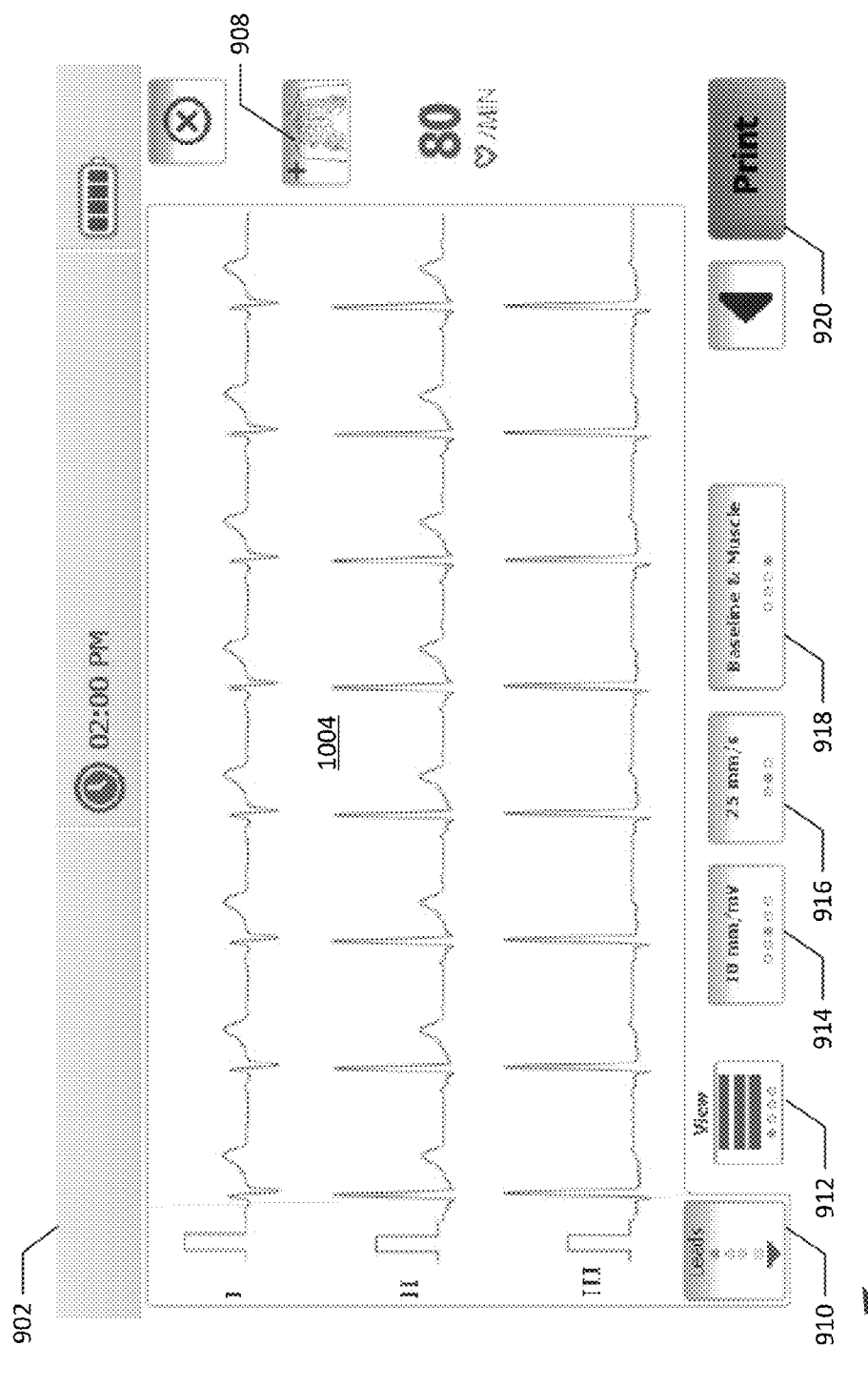
FIG. 10 is an example of the lead display system including a minimized patient torso depiction as in FIG. 8.

FIGS. 9-10 illustrate example versions of a lead display 900 according to the schematic illustrated in FIGS. 7-8, respectively. In particular, FIG. 9 shows a screen layout 902 that includes a common region 904, and an enlarged torso image 906 positioned to the side of that region, alongside a minimized version of the torso image 908. As discussed above with respect to FIGS. 7-8, the screen layout 902 further includes a plurality of navigation and display features alongside a bottom edge of the common region 904, including a leads region 910, a view toggle button 912, a gain adjustment button 914, a speed adjustment button 916, and a filter button 918. The screen layout 902 further includes a print button 920 for capturing a particular waveform.

FIG. 10 illustrates, similar to FIG. 8, a second screen layout 1002, in which the enlarged torso image 904 is removed, leaving only the minimized version of the torso image 908. Accordingly, a larger version of a common region 1004 is displayed. In this arrangement, as with that shown in FIG. 8, a greater number of heartbeat periods can be shown in the common region 1004 on a display, as compared to common region 904 (in the example shown, four such periods are shown in FIG. 9, and eight periods are shown in FIG. 10). Accordingly, a user can quickly select between being able to see a full status of electrodes on a graphical depiction of a patient torso (the enlarged torso image), or a larger number of heart beat periods.

Referring to FIGS. 11-15, additional navigation features are illustrated, allowing for convenient switching among a plurality of different views, each having a different combination of regions displayed. In the examples shown, a view toggle button, such as the buttons 312, 512, 712, or 912, could be used to switch among a plurality of selectable views.

Figure 11:
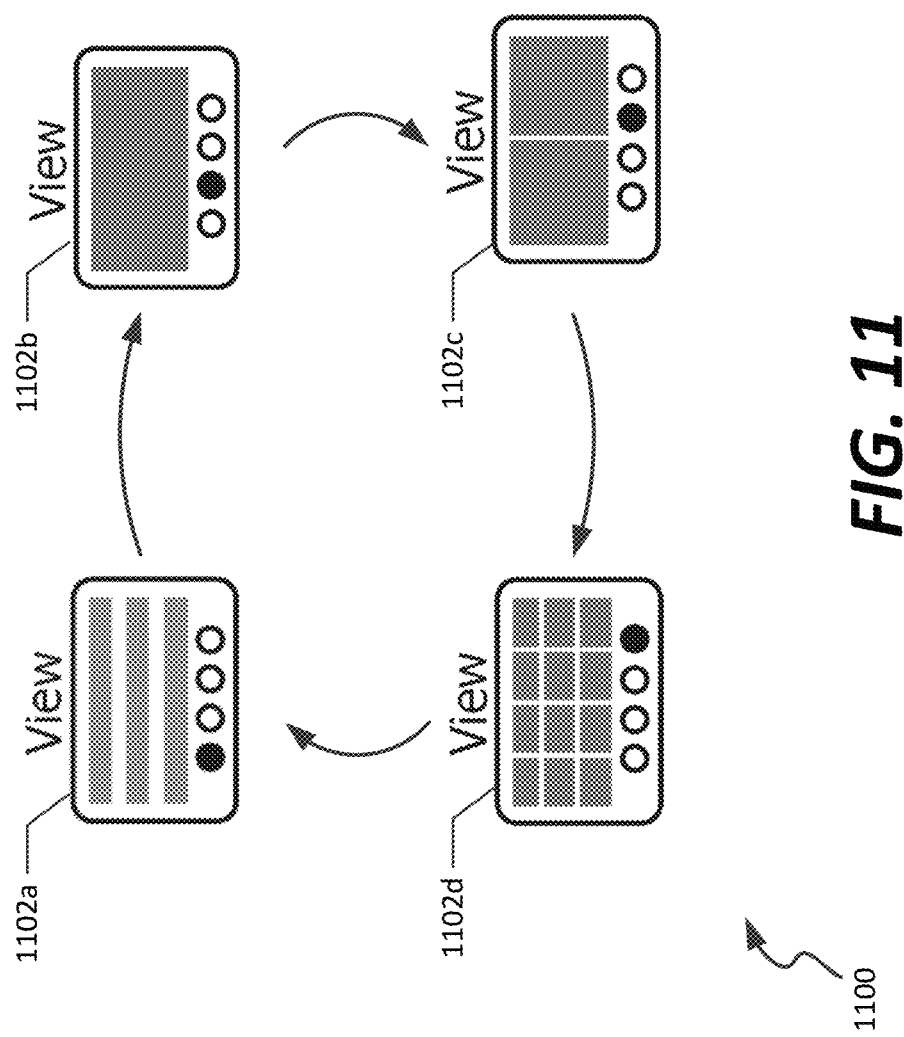
FIG. 11 is a schematic illustration of a sequence of toggling among views of waveforms representing electrical signals at each of a plurality of electrocardiograph signal leads.
Figure 12:
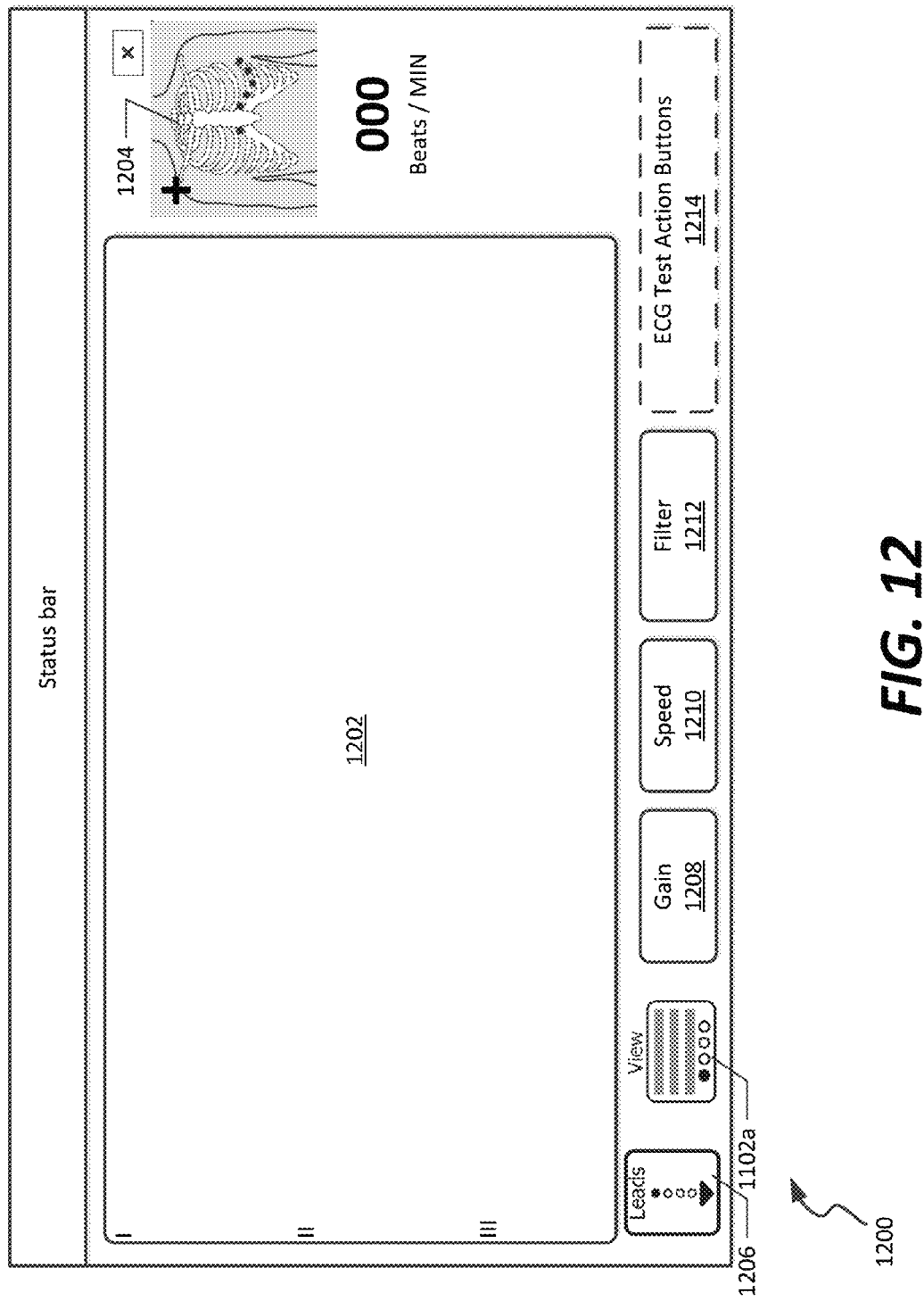
FIG. 12 is a schematic illustration of a first example screen layout among the screen layouts selectable via a view toggle button, according to an example embodiment.
Figure 13:
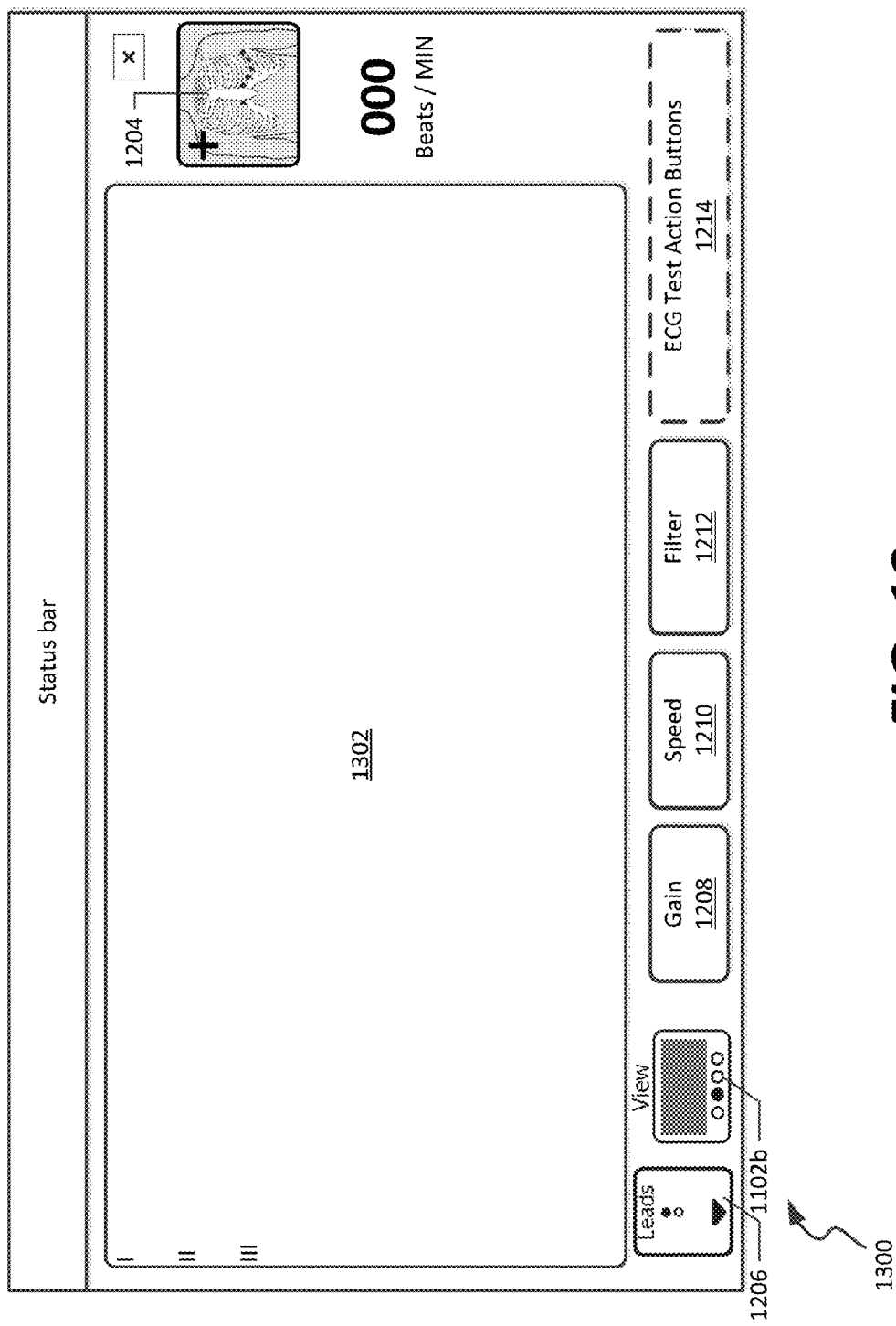
FIG. 13 is a schematic illustration of a second example screen layout among the screen layouts selectable via a view toggle button, according to an example embodiment.
Figure 14:
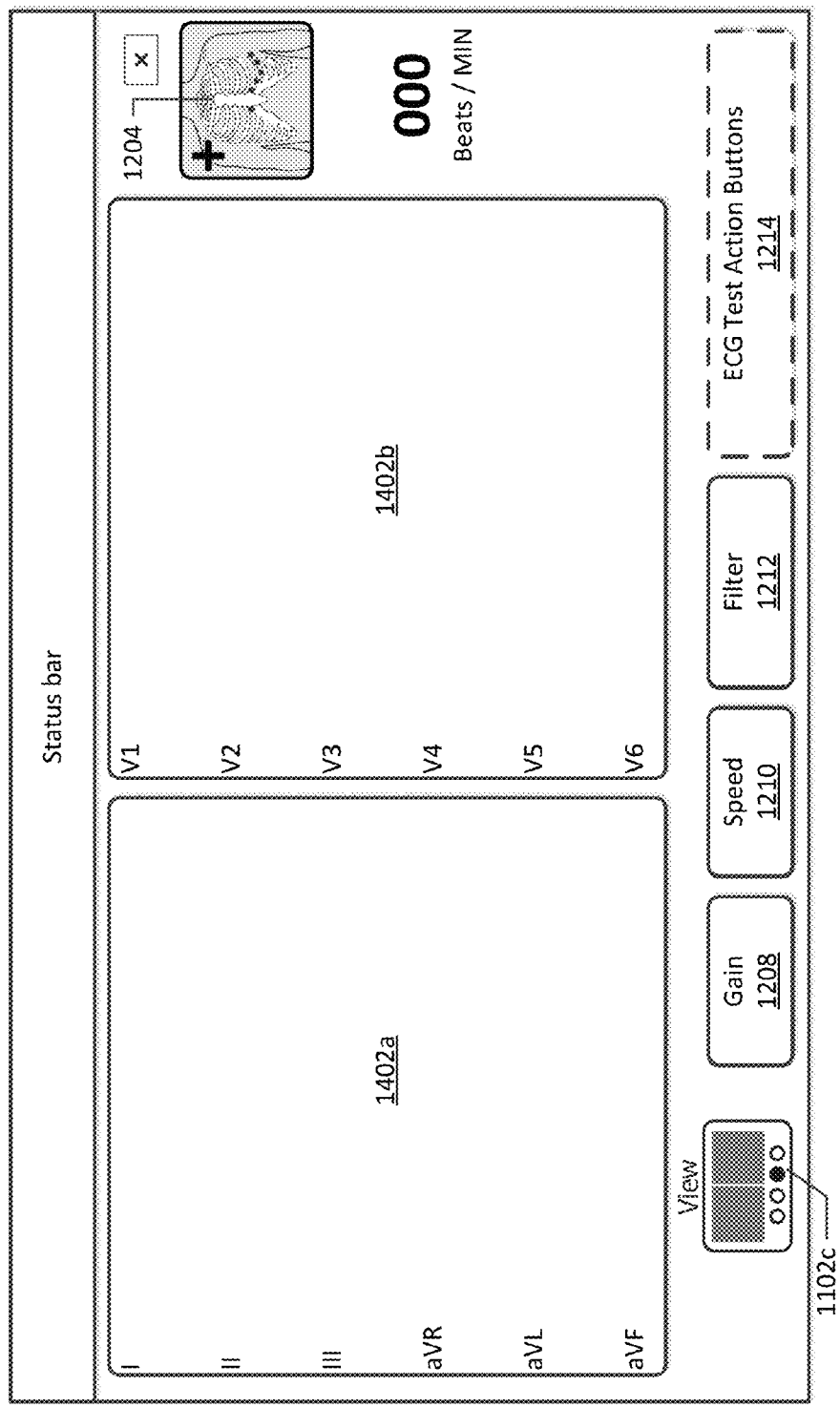
FIG. 14 is a schematic illustration of a third example screen layout among the screen layouts selectable via a view toggle button, according to an example embodiment.
Figure 15:
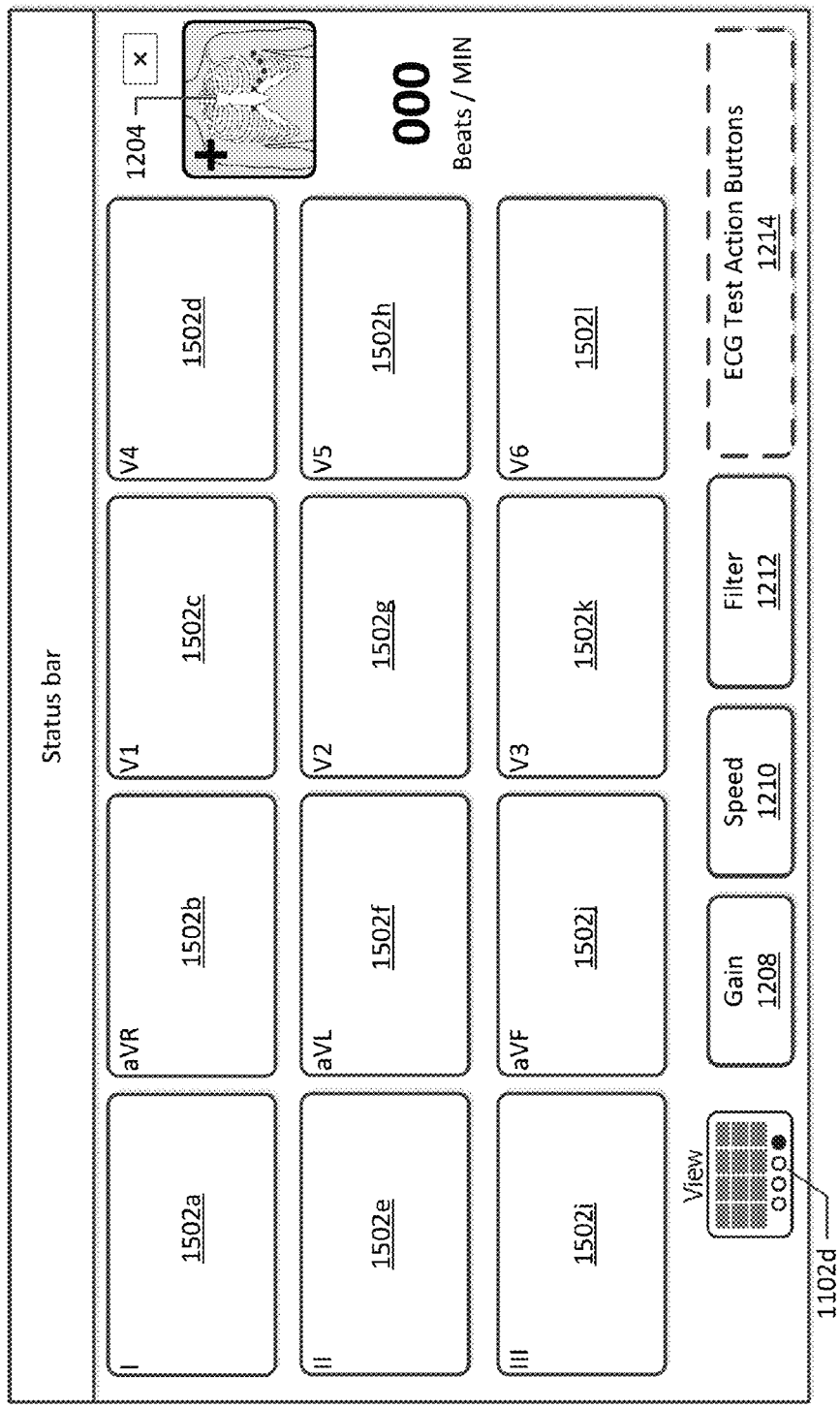
FIG. 15 is a schematic illustration of a fourth example screen layout among the screen layouts selectable via a view toggle button, according to an example embodiment.

FIG. 11 specifically shows one example sequence 1100 of views that can be selected via a view toggle button, shown as toggle buttons 1102a-d (collectively, view toggle button 1102). In the embodiment shown, the view toggle button 1102 can be selected, for example via a touch screen display, to cycle among a plurality of views. As shown, the view toggle button changes appearance to represent the current view; for example, in the various embodiments discussed herein, a first version of the view toggle button 1102, depicted as button 1102a, corresponds to a screen layout 1200 as seen in FIG. 12; a second version, depicted as button 1102b, corresponds to screen layout 1300 as seen in FIG. 13. Similarly, a third version of the view toggle button 1102c, corresponds to a screen layout 1400 as seen in FIG. 14, and a fourth version, depicted as button 1102d, corresponds to screen layout 1500 as seen in FIG. 15. Of course, it is understood that other views, and other corresponding versions of the view toggle button 1102, could be used as well.

As seen in FIG. 12, a first screen layout 1200 includes a region 1202 occupying a majority of the screen area. The first screen layout 1200 also includes a view toggle button 1102a, as well as a variety of other control buttons, and graphical elements, including a patient torso graphic 1204, leads region 1206, a gain adjustment button 1208, speed adjustment button 1210, and filter button 1212. The first screen layout 1200 also includes one or more ECG test action buttons 1214.

Within the first screen layout, the leads region 1206 can be selected to cycle among four different lead graphics, each of which display three lead waveforms within the region 1202. The remaining elements (buttons 1208-1214) operate analogously to those features discussed above in connection with alternative embodiments.

As seen in FIG. 13, a second screen layout 1300 includes a single region 1302 occupying a majority of the screen area, but locates the lead waveforms along a top portion of that region, allowing for other data to be displayed within the region. The second screen layout 1300 further includes a view toggle button 1102b, as well as the various other graphical elements/regions 1204-1214 discussed above.

FIG. 14 illustrates a third screen layout 1400 including a pair of regions 1402a-b, each of which displays six waveforms. The third screen layout 1400 therefore displays waveforms associated with each of the plurality of electrocardiograph signal leads. Accordingly, although the third screen layout includes the patient torso graphic 1204 and buttons 1208-1214, it lacks the leads region 1206, since no leads remain undisplayed. Of course, it is recognized that because the leads are all displayed, a smaller amount of each waveform can be presented on the display. The third screen layout 1400 includes a view toggle button 1102c, allowing for cycling among the various screen layouts discussed herein.

FIG. 15 illustrates a fourth screen layout 1500 including twelve individual regions 1502a-l. The fourth screen layout 1500 includes a view toggle button 1102d, as well as patient torso graphic 1204 and buttons 1208-1214. As with the third screen layout 1400, in the fourth screen layout the leads region is not required, since each of the leads remains displayed.

In use, the view toggle button 1102 cycles through a sequence of states, which correspond to views, or screen layouts, as discussed below. In the example shown, a sequential arrangement of screens is provided in which selection of view toggle button 1102a causes screen layout 1200 to change to screen layout 1300, while selection of view toggle button 1102b causes screen layout 1300 to change to screen layout 1400, selection of view toggle button 1102c causes screen layout 1400 to change to screen layout 1500, and selection of view toggle button 1102d causes screen layout 1500 to change to screen layout 1200, as illustrated in the sequence 1100 of FIG. 11.

Referring to FIGS. 1-15 overall, it is recognized that the various navigation features discussed herein provide a great deal of flexibility and allow for convenient navigation among a variety of screen layouts, or views, of waveforms depicting electrocardiograph signals, as well as the status of leads with which those signals are captured. Additionally, the various features discussed herein allow for convenient and intuitive use in connection with a touch screen display integrated into an ECG device.

Further, in connection with the present disclosure, embodiments of the invention may be practiced in an electrical circuit comprising discrete electronic elements, packaged or integrated electronic chips containing logic gates, a circuit utilizing a microprocessor, or on a single chip containing electronic elements or microprocessors. For example, embodiments of the invention may be practiced via a system-on-a-chip (SOC) where each or many of the components illustrated in FIG. 1 may be integrated onto a single integrated circuit. Such an SOC device may include one or more processing units, graphics units, communications units, system virtualization units and various application functionality all of which are integrated (or "burned") onto the chip substrate as a single integrated circuit. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:
1. An electrocardiograph device comprising:
a display;
a plurality of electrocardiograph signal leads configured for electrical connection to a patient;
a programmable circuit operatively connected to the display and to the plurality of electrocardiograph signal leads, the programmable circuit configured to receive electrical signals via the electrocardiograph signal leads representative of a heartbeat of a patient, wherein the programmable circuit is further configured to:
generate a user interface to be presented on the display, the user interface comprising a lead display including a screen layout including a plurality of waveform regions, the waveform regions being adjacent to one another and each displaying a waveform corresponding to an elec- trical signal from one of the plurality of electrocardiograph signal leads over a first time interval including at least one heartbeat period;

upon receiving selection of a region of the user interface, display an extended waveform region associated with one or more of the electrocardiograph signal leads, the extended waveform region displaying a waveform corresponding to the electrical signal from one of the plurality of electrocardiograph leads over a second time interval that is longer than the first time interval, and which includes a plurality of heartbeat periods;

wherein the lead display includes an image of a torso depicting locations of leads placed on the patient; and wherein one or more of the locations depicted on the torso provide a visual indication of whether or not a signal is being received at that location.

2. The electrocardiograph device of claim 1, wherein the display comprises a touch screen display, and wherein selection of the region comprises touching the region to be selected.

3. The electrocardiograph device of claim 1, wherein the region comprises a view toggle button, wherein, in response to selection of the view toggle button, the lead display cycles among a plurality of views, wherein the extended region is included within at least one of the plurality of views.

4. The electrocardiograph device of claim 3, wherein each of the plurality of views corresponds to a different layout of regions within the lead display.

5. The electrocardiograph device of claim 1, wherein the region comprises one of the plurality of waveform regions.

6. The electrocardiograph device of claim 5, wherein, upon display of the extended waveform region, one or more of the plurality of waveform regions of the lead display are hidden from view.

7. The electrocardiograph device of claim 6, wherein a selection of the extended waveform region reverts the lead display to displaying each of the plurality of waveform regions including the waveform regions hidden from view while the extended waveform region is displayed.

8. The electrocardiograph device of claim 1, wherein the user interface further includes a leads region selectable by a user, wherein, upon receiving selection of the leads region, the programmable circuit is further programmed to display a second screen layout including a plurality of waveform regions including waveform regions corresponding to electrical signals from one or more of the plurality of electrocardiograph signal leads not presented in the lead display.

9. The electrocardiograph device of claim 1, wherein the lead display includes one or more test action buttons.

10. The electrocardiograph device of claim 1, wherein, upon selection of the image of the torso, displaying an enlarged image of the torso overlaying at least a portion of one or more of the plurality of waveform regions.

11. An electrocardiograph device comprising:
a display;
a plurality of electrocardiograph signal leads configured for electrical connection to a patient;
a programmable circuit operatively connected to the display and to the plurality of electrocardiograph signal leads, the programmable circuit configured to receive electrical signals via the electrocardiograph signal leads representative of a heartbeat of a patient, wherein the programmable circuit is further configured to:

generate a user interface to be presented on the display, the user interface comprising a lead display including a screen layout including a plurality of regions, the plurality of regions being adjacent to one another and each displaying an indication of an electrical signal from one or more of the plurality of electrocardiograph signal leads, and the user interface including an image of a torso depicting locations of leads placed on the patient, with one or more of the locations depicted on the torso provide a visual indication of a weak signal through a change in appearance of the visual indication;

upon receiving selection of a region of the user interface, displaying an extended region associated with one or more of the electrocardiograph signal leads, the extended region at least partially overlaying one or more remaining regions adjacent to the selected region.

12. The electrocardiograph device of claim 11, wherein the extended region comprises an enlarged graphical representation of the torso of the patient.

13. The electrocardiograph device of claim 11, wherein the selected region displays a waveform corresponding to an electrical signal from one of the plurality of electrocardiograph signal leads over a first time interval including at least one heartbeat period.

14. The electrocardiograph device of claim 13, wherein the extended region displays a waveform corresponding to the electrical signal from the electrocardiograph signal lead of the selected region over a second time interval that is longer than the first time interval, and which includes a plurality of heartbeat periods.

15. The electrocardiograph device of claim 11, wherein, upon receiving a selection of the extended region, the programmable circuit is configured to revert to the screen layout displaying each of the plurality of regions.

* * * * *